United States Patent
Pazzucconi et al.

(10) Patent No.: US 6,232,517 B1
(45) Date of Patent: May 15, 2001

(54) PROCESS FOR THE PREPARATION OF 2,6-DIMETHYLNAPHTHALENE

(75) Inventors: Giannino Pazzucconi, Broni; Carlo Perego, Carnate; Roberto Millini, Cerro al Lambro; Francesco Frigerio, Torre d'Isola; Riccardo Mansani, Sassari; Daniele Rancati, Porto Torres, all of (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/592,673

(22) Filed: Jun. 13, 2000

Related U.S. Application Data

(62) Division of application No. 09/281,961, filed on Mar. 31, 1999, now Pat. No. 6,147,270.

(30) Foreign Application Priority Data

Apr. 17, 1998 (IT) ............................................. MI98A0809

(51) Int. Cl.[7] ....................................................... C07C 5/22
(52) U.S. Cl. ........................................... 585/481; 585/480
(58) Field of Search ................................... 585/481, 480; 502/77, 71, 64, 61

(56) References Cited

U.S. PATENT DOCUMENTS

| 5,003,122 | 3/1991 | Fellman et al. | 585/467 |
| 5,670,704 | 9/1997 | Hagen et al. | 585/471 |
| 5,672,799 | 9/1997 | Perego et al. | 585/467 |
| 6,034,291 | 3/2000 | Perego et al. | |
| 6,147,270 | 11/2000 | Pazzucconi et al. | |

FOREIGN PATENT DOCUMENTS

| 2 246 788 | 2/1992 | (GB) . |
| WO 90/03960 | 4/1990 | (WO) . |

*Primary Examiner*—Marian C. Knode
*Assistant Examiner*—Thuan D. Dang
(74) *Attorney, Agent, or Firm*—Oblon, Spivak, McClelland, Maier & Neustadt, P.C.

(57) ABSTRACT

A highly selective process is described for preparing 2,6-dimethylnaphthalene which comprises reacting a naphthalene hydrocarbon selected from naphthalene, methylnaphthalenes, dimethylnaphthalenes, trimethylnaphthalenes, polymethylnaphthalenes or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions, in the presence of a zeolite belonging to the structural type MTW and optionally in the presence of a methylating agent.

2 Claims, No Drawings

PROCESS FOR THE PREPARATION OF 2,6-DIMETHYLNAPHTHALENE

This is a Division of application Ser. No. 09/281,961, filed Mar. 31, 1999 now U.S. Pat. No. 6,147,270.

A highly selective process is described for preparing 2,6-dimethylnaphthalene which comprises reacting a naphthalene hydrocarbon selected from naphthalene, methylnaphthalenes, dimethylnaphthalenes, trimethylnaphthalenes, polymethylnaphthalenes or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions, in the presence of a zeolite belonging to the structural type MTW and optionally in the presence of a methylating agent.

2,6-dimethylnaphthalene is an intermediate in the synthesis of 2,6-naphthalenedicarboxylic acid, used as monomer in the preparation of PEN (polyethylnaphthalate). It is known that it can be recovered from fractions coming from the reforming of kerosine (U.S. Pat. No. 4,963,248) or from fractions of FCC oil (European Chemical News, page 30, Sep. 28, 1992). In the first case, the dimethylnaphthalenes must be separated by distillation, then, the 2,6 isomer is isolated by means of selective absorptions and/or crystallization. In the second case, there is an additional problem due to the presence of nitrogen and sulfur which poison the catalysts used for the separation and/or isomerization phases. There is also a process (U.S. Pat. No. 4,990,717; U.S. Pat. No. 5,118,892; U.S. Pat. Nos. 5,073,670; 5,030,781; 5,012,024) which, by means of alkenylation, cyclization, dehydrogenation, isomerization, leads to the selective synthesis of 2,6-dimethylnaphthalene. This high number of passages obviously represents a burden from an economical point of view and in addition, each passage or chemical reaction involves secondary reactions requiring separations to guarantee the purity of the intermediates or end-product. U.S. Pat. No. 5,043,501 describes a synthesis method of 2,6-dimethylnaphthalene in two steps. The first comprises the alkylation of an alkylaromatic with a $C_5$ olefin in the presence of a zeolitic catalyst, the second comprises a dehydrocyclization at 400–500° C. with a catalyst consisting of Pt/Ba/K on zeolite L, obtaining a product containing dimethylnaphthalenes which are then isomerized mainly to 2,6 isomer.

S. B. Pu and T. Inui describe in Applied Catalysis A, General 146 (1996) 305–316, the alkylation with methanol of methylnaphthalene, catalyzed by zeolites of the BEA, FAU and MTW groups, carried out without a solvent and in an exclusively gaseous phase. The best results are obtained with beta zeolite and faujasite. A. S. Loktev and P. S. Chekriy, in Zeolites and Related Micro-porous Materials: State of art 1994, SSSC vol. 84, J. Weitkamp et al. (Eds) describe the alkylation of naphthalene or methylnaphthalene with methanol catalyzed by ZSM-12, carried out in the presence of paraffinic solvents and in gaseous phase. The yields to dimethylnaphthalenes, and to 2,6 isomer in particular, are zero or in any case negligible. In addition, high quantities of heavy by-products are obtained, due to the reaction conditions and/or decomposition of the paraffinic solvents used.

U.S. Pat. No. 4,795,847 discloses a process for the preparation of 2,6-dialkylnaphthalenes which comprises the alkylation in gaseous phase of naphthalene or 2-alkyl-naphthalene with an alkylating agent in the presence of a zeolite selected from mordenite, EU-1, offretite, ZSM-12, ZSM-5 and ZSM-22. In the case of the methylation of naphthalene or 2-methyl-naphthalene the use of ZSM-5 is particularly preferred. To reduce undesired isomerization reactions which result in the formation of 1-alkyl-naphthalene, the zeolitic catalyst is previously subjected to precarbonization treatment. An example is provided of the alkylation of 2-methylnaphthalene with methanol, in gas phase, catalyzed by ZSM-5: the conversion obtained between 0.5 and 8 hours is from 5 to 7%, the yield to dimethylnaphthalenes ranges from 4 to 5% and the 2,6-dimethylnaphthalene isomer forms 50% of the dimethylnaphthalene fraction.

We have now unexpectedly found a process for preparing 2,6-dimethylnaphthalene starting from naphthalene, methylnaphthalenes, dimethylnaphthalenes, trimethylnaphthalenes and/or polymethylnaphthalenes carried out under at least partially liquid phase conditions and in the presence of suitable aromatic hydrocarbons, catalyzed by a zeolite of the structural type MTW (abbreviation IZA), which allows better results to be obtained in terms of yield, selectivity, conversion to useful products in the time unit and life of the catalyst, with respect to what is described in the prior art. In particular MTW zeolites, when used under the conditions of our invention, are more active not only than the same zeolites used under the conditions described previously, but also with respect to the BEA and MFI zeolites already described in the prior art as the best catalysts for the preparation of 2, 6 -dimethylnaphthalene.

The present invention therefore relates to a process for preparing 2,6-dimethylnaphthalene which comprises reacting a naphthalene hydrocarbon selected from naphthalene, methylnaphthalenes, dimethylnaphthalenes, trimethylnaphthalenes, pentamethylnaphthalenes, hexamethylnaphthalenes or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions, in the presence of a zeolite belonging to the structural type MTW and optionally in the presence of a methylating agent.

The naphthalene hydrocarbon is preferably selected from naphthalene, methylnaphthalenes, dimethylnaphthalenes, trimethylnaphthalenes, or their mixtures. A particularly preferred aspect is that the reagent is naphthalene and/or methylnaphthalene, optionally mixed with dimethylnaphthalenes and/or trimethylnaphthalenes.

Fractions containing naphthalene, methylnaphthalenes and dimethylnaphthalenes, obtained by distillation from FOC (Fuel Oil Cracking) or LCO (Light Cycle Oil) cracking oils or obtained by the distillation of distilled oil from pit-coal tar, can be used directly in the process of the present invention.

According to a particularly preferred aspect of the present invention, the process for the preparation of 2,6-dimethylnaphthalene is carried out in the presence of the methylating agent which can be selected from methanol, dimethylether, dimethylcarbonate, dimethylsulfate, methyl iodide. Methanol is preferably used.

Operating according to our invention, a high selectivity is unexpectedly obtained, which, with respect to thermodynamic equilibrium values, is unbalanced towards the 2,6 isomer: there are consequently kinetic control conditions of the reaction. The molar ratio between the 2,6 and 2,7 isomers of dimethynaphthalene can also be considered as selectivity index reached with our invention. Whereas the thermodynamic ratio is about 1 (S. B. Pu and T. Inui, in Applied Catalysis A, General 146 (1996) 305–316) in the case of zeolitic catalysts with an MFI and BEA structure it is 1 and 1.3 respectively, in the case of MTW zeolites used in gas phase it is 1.2 and 1.5, in the case of MTW zeolites used according to our invention, this ratio varies from 1.9 to 2.7.

For evaluating the selectivity which can be reached with our invention, the selectivity to 2,6 or 2,6+1,6 isomer can also be considered. According to the thermodynamic equilibrium (calculated by S. B. Pu and T. Inui, in Applied Catalysis A, General 146 (1996) 305–316) there is 12% of the 2,6 isomer and 14% of the 1,6 isomer. With the process of our invention, values are registered equal to 26–35% for the 2,6 isomer and 25–32% for the 1,6 isomer, depending on the reaction conditions: in any case the values are higher than the thermodynamic ones.

Operating under the conditions of our invention, and in the presence of one or more of the particular benzene hydrocarbons selected, zeolites of the structural type MTW give better results than those of zeolites of the MFI group, not only because they are more active, with a longer life and therefore greater productivity, but because they provide a product containing a higher percentage of 1,6 and 1,5 isomers which can be easily converted to 2,6 isomer by means of commercial processes or known methods such as those for example described in EP 519165 and U.S. Pat. No. 5,012,024. In addition, the MFI zeolites produce significant quantities, which tend to increase with deactivation, of ethylnaphthalene which on the other hand is not revealed by GC analysis among the products obtained according to the process of our invention. With respect to BEA zeolites, the MTW zeolites used according to our invention are more selective, more active, with a longer life and produce less tri and tetra-methylnaphthalenes (with the same conversion).

Zeolites of the MTW structural type which can be used in the present invention are for example: ZSM-12, CZH-5, Nu-13, Theta-3 and TPZ-12.

The zeolite CZH-5 is described in GB 2079735A; Nu-13 is described in EP59059; Theta-3 is described in EP 162719 and TPZ-12 in U.S. Pat. No. 4,557,919.

The zeolite of the MTW structural type which is best suited for use in the present invention is a silico-aluminate with a molar ratio $SiO_2/Al_2O_3$ greater than or equal to 20. This zeolite and its preparation are described in A.Katovic and G.Giordano, Chem. Ind. (Dekker) (Synthesis of Porous Materials) 1997 69, 127–137. The aluminum can be total or partly substituted by B, Ga, Fe or their mixtures as described by Toktarev & Ione, in Chon et al., Progress in Zeolites and Microporous Materials, SSSC, vol. 105, 1997.

According to a preferred aspect the zeolite ZSM-12 is used, a porous crystalline material having in its calcined and anhydrous form a molar composition of oxides corresponding to the following formula:

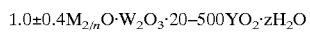
$$1.0\pm 0.4 M_{2/n}O \cdot W_2O_3 \cdot 20{-}500 YO_2 \cdot zH_2O$$

wherein M is $H^+$ and/or a cation of an alkaline or earth alkaline metal with valence n, W is selected from aluminum, gallium or their mixtures, Y is selected from silicon or germanium, z is between 0 and 60. M is preferably selected from sodium, potassium, hydrogen or their mixtures. W is preferably aluminum and Y is preferably silicon. W can be at least partially substituted by boron, iron or their mixtures. The zeolite ZSM-12 is described in U.S. Pat. No. 3,832,449, in Ernst et al., Zeolites, 1987, Vol. 7, September, and in Toktarev & Ione, Chon et al., Progress in Zeolites and Microporous Materials, SSSC, vol. 105, 1997.

A particularly preferred aspect of the present invention is that the zeolite of the MTW type used is in the form in which the cation sites present in its structure are occupied for at least 50% by hydrogen ions. It is particularly preferable for at least 90% of the cation sites to be occupied by hydrogen ions.

The zeolite can be used as such, pelletized in pure form, or extruded with suitable inorganic oxide ligands to form cylindrical, spherical pellets, or with other forms commonly used, or obtained as microspheres by spray-drying after mixing with a ligand. The ligands can be for example, aluminas, silicas, silicoaluminas, titania, zirconia or clays. Alumina is preferably used. In the bound catalyst the zeolite and the ligand are in a weight ratio ranging from 10:90 to 90:10, preferably from 25:75 to 75:25.

The benzene hydrocarbon is selected from benzene, toluene, xylenes, trimethylbenzenes, tetramethylbenzenes, pentamethylbenzene, hexamethylbenzene or their mixtures, and is preferably trimethylbenzene. It is obviously necessary to operate in the presence of the methylating agent when only benzene is used as benzene hydrocarbon together with naphthalene alone as naphthalene substrate. The process of the present invention is completely different from the known simple alkylation processes of the prior art: in fact it is the result of contemporaneous transalkylation, deproportioning, isomerization and alkylation reactions in which all the types of methyl present in the reaction mixture unexpectedly participate, directly or indirectly, in the methylation of the naphthalene substrate used and contribute to obtaining very high selectivities. Methyls present in the reaction mixture refer to both those deriving from benzene hydrocarbon and also those possibly already present on one or more of the naphthalene substrates used.

In accordance with this, at the end of the process, the benzene hydrocarbon or mixture of benzene hydrocarbons used will produce a mixture of corresponding benzene hydrocarbons differently methylated both quantitatively and qualitatively, arising from the processes mentioned above. The best results are obtained when a methylating agent is used and consequently at least part of the methyls which are found in the 2,6-dimethylnaphthalene end-product derive directly or indirectly from this, i.e. by alkylation on the part of the methylating agent of the aromatic hydrocarbon and subsequent transalkylation on the naphthalene substrate.

The feeding of the benzene hydrocarbon is such as to obtain a molar ratio between the hydrocarbon and naphthalene groups ranging from 1 to 100, more preferably from 3 to 20, naphthalene groups referring to the naphthalene hydrocarbon used as substrate or, when several naphthalene hydrocarbons are present, the sum of their moles.

When the process of the present invention is carried out in the presence of a methylating agent, preferably methanol, a molar ratio between methylating agent and the naphthalene groups of less than 30 is used, preferably ranging from 0.1 to 3.

The reaction temperature ranges from 200° C. to 450° C., preferably from 250 to 390° C., even more preferably from 280 to 350° C., the WHSV space velocity ranges from 0.01 to 8 hours$^{-1}$, preferably from 0.05 to 1 hours$^{-1}$.

It should be pointed out that the combination of temperature and pressure conditions used should be such as to guarantee that the synthesis of the 2,6-dimethylnaphthalene at least partly takes place in liquid phase, and even more preferably substantially in liquid phase.

The pressure used can vary from 3 to 60 atm.

The process of the present invention can be industrially carried out in continuous, semicontinuous or batch; in order to keep the temperature within a preferred range, the catalyst can be arranged in the reactor in various layers. A quench with naphthalene, with the hydrocarbon or mixture of benzene hydrocarbons used in the process itself, or with the methylating agent, preferably methanol, when present, can be carried out between one layer and another.

The temperature control can be carried out not only by means of a quench of the reagents and/or inert products, but also by intercooling between the layers, for example by means of the interpositioning of coolants. The synthesis of 2,6-dimethylnaphthalene can be conveniently carried out either in a reactor in which the catalyst is arranged in two or more beds or in two or more reactors in series, intercooled to control the temperature.

When an alkylating agent is used, it can be fed in two or more steps. The alkylating agent is preferably fed in two or more steps along the catalytic beds of the reactor or between these, and/or between the reactors situated in series.

According to a preferred aspect, in order to maximize the production of 2,6-dimethylnaphthalene, the product obtained according to the process of the present invention can be separated into:
(a) a fraction containing benzene hydrocarbons, naphthalene and methylnaphthalene, (b) a fraction containing dimethylnaphthalenes and (c) a fraction containing polymethylated naphthalenes. The desired 2,6-dimethylnaphthalene isomer is isolated from the fraction (b) of dimethylnaphthalenes, whereas the remaining fraction (d) containing dimethylnaphthalenes different from the 2,6 isomer, and fractions a) and c), are re-fed to the initial reactor where they re-enter the reactive cycle. Alternatively, fraction (d) and fractions (a) and (c), optionally enriched with naphthalene and/or methylnaphthalene, can be fed to a specific reactor where they are reacted, under at least partially liquid phase conditions, in the presence of a zeolite belonging to the MTW structural type, with one or more benzene hydrocarbons selected from benzene, toluene, xylenes, trimethylbenzenes, tetramethylbenzenes, pentamethylbenzenes and/or hexamethylbenzene. The reaction temperature ranges from 200 to 450° C., and the space velocity ranges from 0.01 to 8 hours$^{-1}$.

According to another aspect of the present invention, to maximize the production of 2,6-methylnaphthalene, fraction (d) containing dimethylnaphthalenes different from 2,6-dimethylnaphthalene, in particular the 1,6 and 1,5 isomer, is subjected to isomerization, under at least partially liquid phase conditions, in the presence of a catalyst containing an MTW zeolite, at a temperature ranging from 100 to 400° C., more preferably from 120 to 250° C., even more preferably from 130 to 200° C.

This particular isomerization process of 1,6-dimethylnaphthalene and 1,5-dimethylnaphthalene, pure or mixed with other dimethylnaphthalene isomers, to give 2,6-dimethylnaphthalene, catalyzed by a zeolite of the MTW type, is in itself innovative and represents a further object of the present invention.

The exhausted catalyst deriving from the process for preparing 2,6-dimethylnaphthalene can be regenerated with the known combustion methods of coke or of its precursors to which the deactivation of the solid acid materials which catalyze reactions involving hydrocarbons, is due. We have also unexpectedly found a method for regenerating this exhaused catalyst, which is much simpler and more economical. This new method does not require, with respect to the traditional regenerative methods, either removal of the catalyst from the reaction environment or the high temperatures necessary for the combustion of coke. A further object of the present invention therefore relates to a method for regenerating the exhausted catalyst deriving from the process for the preparation of 2,6-dimethylnaphthalene by the reaction of a naphthalene hydrocarbon selected from naphthalene, methylnaphthalenes, dimethylnaphthalenes, trimethylnaphthalenes, tetramethylnaphthalenes, pentamethylnaphthalenes, hexamethylnaphthalene or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions, in the presence of a zeolite belonging to the MTW structural type and optionally in the presence of a methylating agent, wherein said regeneration method comprises treating the exhausted catalyst with one or more of these benzene hydrocarbons, at a temperature ranging from 200 to 450° C., more preferably from 250 to 400° C., even more preferably from 280 to 370° C., said temperature being at least equal to that used during the preparation process of 2,6-dimethylnaphthalene from which the exhausted catalyst derives. The regeneration conditions are selected so as to operate in at least partially liquid phase, the WHSV space velocity can range from 0.01 to 8 hours$^{-1}$ and the pressure can be selected from 5 to 60 atm.

EXAMPLE 1

Preparation of the Catalyst ZSM-12

2.4 grams of sodium aluminate at 56% of $Al_2O_3$ are dissolved in 84 grams of aqueous solution of tetraethylammonium hydroxide at 35%. The limpid solution thus obtained is poured, under stirring, into 200 grams of colloidal silica Ludox HS 40. After brief stirring a limpid and homogeneous gel is obtained which is poured into an AISI316 steel autoclave equipped with an anchor stirrer. The gel is left to crystallize under hydrothermal conditions at 165° C. for 90 hours.

At this point the autoclave is cooled and the solid separated from the mother liquor and washed with demineralized water until the washing water has a pH of less than 9.

The solid is calcined at 550° C. in an atmosphere of air for 5 hours. It is then suspended in a solution of demineralized water and ammonium acetate, the latter in a molar quantity in excess, in particular 5 times, with respect to the aluminum formally present from the synthesis. During this operation the sodium contained from the synthesis in the zeolite is substituted with the ammonium ion by ion exchange effect. This first exchange is followed by a washing, a second exchange using the same procedure and another washing. The solid is then definitely separated from the aqueous environment, dried and calcined for 5 hours at 550° C. in an atmosphere of air. The zeolitic catalyst is thus obtained in acid form. XRD analysis is carried out on the end-sample which shows the presence of only zeolitic crystalline phase of the MTW type, together with a chemical analysis on the basis of which the residual sodium content proves to be less than 50 ppm and the molar ratio $SiO_2/Al_2O_3$ is 100.

EXAMPLE 2

2 gr of ZSM-12 zeolite of example 1 (molar ratio $SiO_2/Al_2O_3$=100) pelleted and granulated within a range of 20–40 mesh, are charged into the isothermal zone of a fixed bed reactor, with quartz above and below as inert filling. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 40 bars.

The mixture of reagents fed consists of 1,2,4-trimethylbenzene, naphthalene, methanol in the following molar ratios: 1,2,4-trimethylbenzene/naphthalene=10, methanol/naphthalene=3. At this point the mixture is heated and brought to a temperature of 350° C. In this test the conditions are therefore liquid phase, with respect to the state of reagents and products. The WHSV (hours$^{-1}$) with respect to the total mixture is 0.86.

The products leaving the reactor are cooled and analyzed by gaschromatography. Samples are taken of the products at regular time intervals (time on stream). The conversion of the methanol is always total.

a) The conversion of naphthalene after 28.2 hours is equal to 85.3%

The selectivities of each product with respect to the naphthalene, defined as ratio between the moles of said product formed and the moles of naphthalene converted, are:
- selectivity dimethylnaphthalenes (% moles): 54.3
- selectivity 2,6-dimethylnaphthalene (% moles): 16.0
- selectivity 2,6/1,6/1,5-dimethylnaphthalene (% moles): 33.4
- selectivity methylnaphthalenes (% moles): 34.6
- selectivity polymethylnaphthalenes (% moles): 11.2
- molar ratio 2,6-dimethylnaphthalene/total dimethylnaphthalenes (% moles): 29.4 (the thermodynamic isomerical distribution, as described in S. B. Pu and T. Inui, Applied Catalysis A, General 146 (1996) 305–316, foresees 12.0% of 2,6 isomer).
- molar ratio 2,6-1,6-1,5-dimethylnaphthalene/total dimethylnaphthalenes (% moles): 61.5 (thermodynamic ratio 32%)
- molar ratio 2,6/2,7 dimethylnaphthalene: 1.9 (thermodynamic ratio 1)

b) The conversion of naphthalene after 95.5 hours is equal to 50.8%

The selectivities with respect to naphthalene are:
- selectivity dimethylnaphthalenes (% moles): 32.5
- selectivity 2,6-dimethylnaphthalene (% moles): 9.0
- selectivity 2,6/1,6/1,5-dimethylnaphthalene (% moles): 18.6
- selectivity methylnaphthalenes (% moles): 64.6
- selectivity polymethylnaphthalenes (% moles): 2.9
- molar ratio 2,6-dimethylnaphthalene/total dimethylnaphthalenes (% moles): 27.5
- molar ratio 2,6-1,6-1,5-dimethylnaphthalene/total dimethylnaphthalenes (% moles): 57.2
- molar ratio 2,6/2,7 dimethylnaphthalene: 2.0 c) The test is then carried out halving the space velocity. The conversion of naphthalene after 102 hours is equal to 59.4%

The selectivities with respect to naphthalene are:
- selectivity dimethylnaphthalenes (% moles): 38.2
- selectivity 2,6-dimethylnaphthalene (% moles): 10.8
- selectivity 2,6/1,6/1,5-dimethylnaphthalene (% moles): 22.5
- selectivity methylnaphthalenes (% moles): 56.7
- selectivity polymethylnaphthalenes (% moles): 5.1
- molar ratio 2,6-dimethylnaphthalene/total dimethylnaphthalenes (% moles): 28.3
- molar ratio 2,6-1,6-1,5-dimethylnaphthalene/total dimethylnaphthalenes (% moles): 59.0
- molar ratio 2,6/2,7 dimethylnaphthalene: 2.0

EXAMPLE 3

4 gr of ZSM-12 zeolite (molar ratio $SiO_2/Al_2O_3$=100), prepared in accordance with example 1, pelleted and granulated within a range of 20–40 mesh, are charged into the isothermal zone of a fixed bed reactor, with quartz above and below as inert filler. The reactor is heated to 200° C. for at least 2 hours, under a stream of nitrogen against atmospheric pressure.

Maintaining under a stream of inert gas, the reactor is cooled to room temperature, and the reagents are then fed until the reactor is pressurized to 35 bars.

The mixture of reagents fed consists of 1,2,4-trimethylbenzene, naphthalene, methanol in the following molar ratios: 1,2,4-trimethylbenzene/naphthalene=18, methanol/naphthalene=2. At this point the mixture is heated and brought to a temperature of 320° C. In this test the conditions are therefore liquid phase, with respect to the state of reagents and products. The WHSV (hours$^{-1}$) with respect to the total mixture is 0.43.

The products leaving the reactor are cooled and analyzed by gaschromatography. Samples are taken of the products at regular time intervals (time on stream). The conversion of the methanol is always total.

a) The conversion of naphthalene after 91 hours is equal to 66.5%

The selectivities with respect to naphthalene are:
- selectivity dimethylnaphthalenes (% moles): 41.2
- selectivity 2,6-dimethylnaphthalene (% moles): 13.0
- selectivity 2,6/1,6/1,5-dimethylnaphthalene (% moles): 26.8
- selectivity methylnaphthalenes (% moles): 53.7
- selectivity polymethylnaphthalenes (% moles): 5.1
- molar ratio 2,6-dimethylnaphthalene/total dimethylnaphthalenes (% moles): 31.5 (the thermodynamic isomeric distribution foresees 12.0% of 2,6 isomer)
- molar ratio 2,6-1,6-1,5-dimethylnaphthalene/total dimethylnaphthalenes (% moles): 65.1 (thermodynamic ratio 32%)
- molar ratio 2,6/2,7 dimethylnaphthalene: 2.1 (thermodynamic 1)

b) The conversion of naphthalene after 241 hours is equal to 59.1%

The selectivities with respect to naphthalene are:
- selectivity dimethylnaphthalenes (% moles): 36.8
- selectivity 2,6-dimethylnaphthalene (% moles): 11.2
- selectivity 2,6/1,6/1,5-dimethylnaphthalene (% moles): 23.3
- selectivity methylnaphthalenes (% moles): 58.9
- selectivity polymethylnaphthalenes (% moles): 4.3
- molar ratio 2,6-dimethylnaphthalene/total dimethylnaphthalenes (% moles): 30.5
- molar ratio 2,6-1,6-1,5-dimethylnaphthalene/total dimethylnaphthalenes (% moles): 63.3
- molar ratio 2,6/2,7 dimethylnaphthalene: 2.3 c) At this point, in order to regenerate the catalyst only 1,2,4-trimethylbenzene is sent to the reactor at a WHSV of 1.32 hours$^{-1}$ and a temperature of 360° C. (under liquid phase conditions, pressure of 35 bars) for 24 hours. The temperature is then brought to 320° C. and the initial mixture with naphthalene and methanol is fed again. After 310 hours of running (of which 286 hours under a stream also containing naphthalene) a sample is taken from the reactor and analyzed, as described above. The conversion of naphthalene after 310 hours is equal to 70.9%

The selectivities with respect to naphthalene are:
- selectivity dimethylnaphthalenes (% moles): 45.7 selectivity 2,6-dimethylnaphthalene (% moles): 14.4
selectivity 2,6/1,6/1,5-dimethylnaphthalene (% moles): 29.9
selectivity methylnaphthalenes (% moles): 47.9
selectivity polymethylnaphthalenes (% moles): 6.4
molar ratio 2,6-dimethylnaphthalene/total dimethylnaphthalenes (% moles): 31.5
molar ratio 2,6-1,6-1,5-dimethylnaphthalene/total dimethylnaphthalenes (% moles): 65.4
molar ratio 2,6/2,7 dimethylnaphthalene: 2.3

The washing with only benzene hydrocarbon unexpectedly allowed recovery of the catalytic activity, without resorting to the methods normally used in the field of the combustion catalysis of coke or its precursors, which is typically responsible for the deactivation of a solid acid which catalyzes reactions involving hydrocarbons.

EXAMPLE 4

4 gr of ZSM-12 zeolite (molar ratio $SiO_2/Al_2O_3=100$), prepared as in example 1, pelleted and granulated within a range of 20–40 mesh, are charged into the isothermal zone of a fixed bed reactor, with quartz above and below as inert filling. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 35 bars. The mixture of reagents fed consists of 1,2,4-trimethylbenzene, naphthalene, methanol in the following molar ratios: 1,2,4-trimethylbenzene/naphthalene=18, methanol/naphthalene=2. At this point the mixture is heated and brought to a temperature of 300° C. In this test the conditions are therefore liquid phase, with respect to the state of reagents and products. The WHSV ($hours^{-1}$) with respect to the total mixture is 0.43.

The products leaving the reactor are cooled and analyzed by gaschromatography. Samples are taken of the products at regular time intervals (time on stream).

The conversion of the methanol is always total.
a) The conversion of naphthalene after 147 hours is equal to 46.6%
The selectivities with respect to naphthalene are:
selectivity dimethylnaphthalenes (% moles): 30.6
selectivity 2,6-dimethylnaphthalene (% moles): 9.7
selectivity 2,6/1,6/1,5-dimethylnaphthalene (% moles): 19.8
selectivity methylnaphthalenes (% moles): 69.4
selectivity polymethylnaphthalenes (% moles): 0.0
molar ratio 2,6-dimethylnaphthalene/total dimethylnaphthalenes (% moles): 31.7 (the thermodynamic isomeric distribution foresees 12.0% of 2,6 isomer)
molar ratio 2,6-1,6-1,5-dimethylnaphthalene/total dimethylnaphthalenes (% moles): 64.8 (thermodynamic ratio 32%)
molar ratio 2,6/2,7 dimethylnaphthalene: 2.5 (thermodynamic 1)
b) The conversion of naphthalene after 506 hours is equal to 28.2%
The selectivities with respect to naphthalene are:
selectivity dimethylnaphthalenes (% moles): 17.9
selectivity 2,6-dimethylnaphthalene (% moles): 6.1
selectivity 2,6/1,6/1,5-dimethylnaphthalene (% moles): 11.7
selectivity methylnaphthalenes (% moles): 80.0
selectivity polymethylnaphthalenes (% moles): 2.0
molar ratio 2,6-dimethylnaphthalene/total dimethylnaphthalenes (% moles): 34.2
molar ratio 2,6-1,6-1,5-dimethylnaphthalene/total dimethylnaphthalenes (% moles): 65.4
molar ratio 2,6/2,7 dimethylnaphthalene: 2.8
c) At this point, in order to regenerate the catalyst only 1,2,4-trimethylbenzene is sent to the reactor at a WHSV of 1.32 $hours^{-1}$ and a temperature of 320° C. (under liquid phase conditions, pressure of 35 bars) for 60 hours. The temperature is then brought to 300° C. and the initial mixture with naphthalene and methanol is fed again. After 600 hours of running (of which 540 hours under a stream also containing naphthalene) a sample is taken from the reactor and analyzed, as described above. The conversion of naphthalene after 600 hours is equal to 43.6%
The selectivities with respect to naphthalene are:
selectivity dimethylnaphthalenes (% moles): 32.4
selectivity 2,6-dimethylnaphthalene (% moles): 9.7
selectivity 2,6/1,6/1,5-dimethylnaphthalene (% moles): 20.8
selectivity methylnaphthalenes (% moles): 67.6
selectivity polymethylnaphthalenes (% moles): 0.0
molar ratio 2,6-dimethylnaphthalene/total dimethylnaphthalenes (% moles): 30.0
molar ratio 2,6-1,6-1,5-dimethylnaphthalene/total dimethylnaphthalenes (% moles): 64.2
molar ratio 2,6/2,7 dimethylnaphthalene: 2.5

Also in this case, washing with only benzene hydrocarbon unexpectedly allowed recovery of the catalytic activity, without resorting to the methods normally used in the field of the combustion catalysis of coke or its precursors, which is typically responsible for the deactivation of a solid acid which catalyzes reactions involving hydrocarbons.

EXAMPLE 5 (comparative)

2 gr of beta zeolite (molar ratio $SiO_2/Al_2O_3=20$), prepared in accordance with U.S. Pat. No. 3,308,069, pelleted and granulated within a range of 20–40 mesh, are charged into the isothermal zone of a fixed bed reactor, with quartz above and below as inert filler. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1,2,4-trimethylbenzene, naphthalene, methanol in the following molar ratios: 1,2,4-trimethylbenzene/naphthalene=10, methanol/naphthalene=3. At this point the mixture is heated and brought to a temperature of 350° C. In this test the conditions are therefore liquid phase, with respect to the state of reagents and products. The WHSV ($hours^{-1}$) with respect to the total mixture is 0.86. The products leaving the reactor are cooled and analyzed by gaschromatography. Samples are taken of the products at regular time intervals (time on stream). The conversion of the methanol is always total.

The conversion of naphthalene after 95 hours is equal to 26.1%
The selectivities with respect to naphthalene are:
selectivity dimethylnaphthalenes (moles): 9.9
selectivity 2,6-dimethylnaphthalene (% moles): 2.5
selectivity 2,6/1,6/1,5-dimethylnaphthalene (% moles): 4.8
selectivity methylnaphthalenes (% moles): 77.5 selectivity polymethylnaphthalenes (% moles): 12.6 molar ratio 2,6-dimethylnaphthalene/total dimethylnaph-
thalenes (% moles): 25.6 molar ratio 2,6-1,6-1,5-dimethylnaphthalene/total dim-
ethylnaphthalenes (% moles): 48.9 molar ratio 2,6/2,7 dimethylnaphthalene: 1.3

From the results indicated above, it can be observed that beta zeolite, under the same conditions as zeolite ZSM-12, is less active, less selective to dimethylnaphthalenes, less selective to 2,6 isomer and 2,6-+1,6-+1,5-isomers, on the contrary beta zeolite is more selective with respect to the formation of the undesired products tri- and tetramethyl-naphthalenes and is less favourable towards the formation of 2,6 isomer with respect to the 2,7 isomer.

EXAMPLE 6 (comparative)

2.3 gr of zeolite ZSM-5 (MFI) (PQ CBU3070E, molar ratio $SiO_2/Al_2O_3=30$), in acid form, pelleted and granulated within a range of 20–40 mesh, are charged into the isothermal zone of a fixed bed reactor, with a quartz above and below as inert filler. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1,2,4-trimethylbenzene, naphthalene, methanol in the following molar ratios: 1,2,4-trimethylbenzene/naphthalene=10, methanol/naphthalene=3. At this point the mixture is heated and brought to a temperature of 450° C. In this test the conditions are therefore gas phase. The WHSV (hours$^{-1}$) with respect to the total mixture is 0.75. The products leaving the reactor are cooled and analyzed by gaschromatography. Samples are taken of the products at regular time intervals (time on stream). The conversion of the methanol is always total.

a) The conversion of naphthalene after 96 hours is equal to 21.8%

The selectivities with respect to naphthalene are:

selectivity dimethylnaphthalenes (% moles): 7.8 selectivity 2,6-dimethylnaphthalene (% moles): 3.6 selectivity 2,6/1,6/1,5-dimethylnaphthalene (% moles): 3.6 selectivity methylnaphthalenes (% moles): 78.3 selectivity polymethylnaphthalenes (% moles): 0.0 selectivity to ethylnaphthalenes (% moles): 14.0 molar ratio 2,6-dimethylnaphthalene/total dimethylnaph-
thalenes (% moles): 26.3 molar ratio 2,6-1,6-1,5-dimethylnaphthalene/total dim-
ethylnaphthalenes (% moles): 46.3 molar ratio 2,6/2,7 dimethylnaphthalene: 0.9

From the results indicated above, it can be observed that zeolite ZSM-5 is less active than ZSM-12. In fact, to have comparable conversions the ZSM-5 must be used at much higher temperatures (450° C. against 350° C.) and under gas phase conditions. As well as being less active, zeolite ZSM-5 is more rapidly deactivated, with a considerable formation of carbonaceous residues, it is less selective to dimethylnaphthalenes, less selective to 2,6 isomer and to 2,6-+1,6-+1,5-isomers. ZSM-5 also produces a significant quantity of undesired ethylnaphthalenes, whereas the molar ratio between the 2,6 and 2,7 isomers of dimethylnaphthalene is practically the thermodynamic ratio and it is not unbalanced towards the 2,6 isomer, which is the isomer of particular interest.

EXAMPLE 7 (comparative)

2 gr of zeolite ZSM-12 (MTW), prepared in accordance with example 1, pelleted and granulated within a range of 20–40 mesh, are charged into the isothermal zone of a fixed bed reactor, with quartz above and below as inert filler. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 30 bars. The mixture of reagents fed consists of 1,2,4-trimethylbenzene, naphthalene, methanol in the following molar ratios: 1,2,4-trimethylbenzene/naphthalene=10, methanol/naphthalene=3. At this point the mixture is heated and brought to a temperature of 400° C. In this test the conditions are therefore gas phase. The WHSV (hours$^{-1}$) with respect to the total mixture is 0.86. The products leaving the reactor are cooled and analyzed by gaschromatography. Samples are taken of the products at regular time intervals (time on stream). The conversion of the methanol is always total.

a) The conversion of naphthalene after 28.5 hours is equal to 76.7%

The selectivities with respect to naphthalene are:

selectivity dimethylnaphthalenes (% moles): 42.5 selectivity 2,6-dimethylnaphthalene (% moles): 10.5 selectivity 2,6/1,6/1,5-dimethylnaphthalene (% moles): 22.1 selectivity methylnaphthalenes moles): 44.0 selectivity polymethylnaphthalenes (% moles): 13.6 molar ratio 2,6-dimethylnaphthalene/total dimethylnaph-
thalenes (% moles): 24.6 (it should be remembered that the thermodynamic isomeric distribution estimates 12.0% of 2,6 (PU))

molar ratio 2,6-1,6-1,5-dimethylnaphthalene/total dim-
ethylnaphthalenes (% moles): 52.1 (thermodynamic 32%)

molar ratio 2,6/2,7 dimethylnaphthalene: 1.5 (thermodynamic 1)

The test is continued and the conversion of naphthalene after 95 hours is equal to 21.0%

The selectivities with respect to naphthalene are:

selectivity dimethylnaphthalenes (% moles): 20.1 selectivity 2,6-dimethylnaphthalene (% moles): 4.1 selectivity 2,6/1,6/1,5-dimethylnaphthalene (% moles): 8.2 selectivity methylnaphthalenes (% moles): 78.3 selectivity polymethylnaphthalenes (% moles): 1.7 molar ratio 2,6-dimethylnaphthalene/total dimethylnaph-
thalenes (% moles): 20.6 (it should be remembered that the thermodynamic isomeric distribution estimates 12.0% of 2,6 (PU))

molar ratio 2,6-1,6-1,5-dimethylnaphthalene/total dim-
ethylnaphthalenes (% moles): 40.7 (thermodynamic 32%)

molar ratio 2,6/2,7 dimethylnaphthalene: 1.2 (thermodynamic 1)

It is further demonstrated that operating in gas phase provides worse performances both in terms of the deactivation rate of the catalyst and selectivity to 2,6 isomer and 2,6-+1,6-+1,5 isomers. The formation of 2,6 isomer with respect to 2,7 isomer is also less favourable.

EXAMPLE 8 (comparative)

4 gr of zeolite ZSM-12 (molar ratio $SiO_2/Al_2O_3=100$), prepared in accordance with example 1, pelleted and granulated within a range of 20–40 mesh, are charged into the isothermal zone of a fixed bed reactor, with quartz above and below as inert filler. The reactor is heated to 200° C. for at least 2 hours, under a stream of nitrogen against atmospheric pressure. Maintaining under a stream of inert gas, the reactor is heated to a temperature of 320° C., and the reagents are then fed into the reactor at atmospheric pressure. The reaction therefore takes place under gas phase conditions. The mixture of reagents fed consists of methylnaphthalenes and methanol in the following ratios: 2-methylnaphthalene/1-methylnaphthalene=1.5; methanol/methylnaphthalenes=0.1.

The WHSV (hours$^{-1}$) with respect to the total mixture is 0.20. The products leaving the reactor are cooled and analyzed by gaschromatography. Samples are taken of the products at regular time intervals (time on stream).

The conversion of the methanol is always total.
a) The conversion of methylnaphthalene after 3 hours is equal to 13.56%

The selectivities with respect to converted methylnaphthalene are:
selectivity dimethylnaphthalenes (% moles): 70.0
selectivity 2,6-dimethylnaphthalene (% moles): 7.3
selectivity 2,6/1,6/1,5-dimethylnaphthalene (% moles): 19.7
selectivity naphthalene (% moles): 11.2
selectivity trimethylnaphthalenes (% moles): 13.5
selectivity heavy products (% moles) 5.3
molar ratio 2,6-dimethylnaphthalene/total dimethylnaphthalenes (% moles): 10.5
molar ratio 2,6-1,6-1,5-dimethylnaphthalene/total dimethylnaphthalenes (% moles): 28.1
molar ratio 2,6/2,7 dimethylnaphthalene: 1.2

The test is continued and the conversion of methylnaphthalene after 24 hours is equal to 3.0%
The selectivities with respect to methylnaphthalene are:
selectivity dimethylnaphthalenes (% moles): 94.6
selectivity 2,6-dimethylnaphthalene (% moles): 9.2
selectivity 2,6/1,6/1,5-dimethylnaphthalene (% moles): 24.4
selectivity methylnaphthalenes (% moles): 1.9
selectivity trimethylnaphthalenes (% moles): 3.2
selectivity heavy products (% moles): 0.3
molar ratio 2,6-dimethylnaphthalene/total dimethylnaphthalenes (% moles): 9.7
molar ratio 2,6-1,6-1,5-dimethylnaphthalene/total dimethylnaphthalenes (% moles): 25.8
molar ratio 2,6/2,7 dimethylnaphthalene: 1.3 (thermodynamic 1)

It is evident that the preparation of 2,6-dimethylnaphthalene under the conditions of the prior art, i.e. under gas phase conditions and without a solvent, causes a precocious and significant deactivation of the catalyst.

The selectivity to total dimethylnaphthalenes is high, but only when coinciding with very low conversions of methylnaphthalene and with a deactivated catalyst.

The distribution of the isomers among the dimethylnaphthalenes is different from that obtained when operating according to the process of the present invention: in particular the molar ratio between the 2,6 isomer and total dimethylnaphthalenes is much lower (10 against 30–35), as is also that between 2,6+1,6 +1,5 and the total dimethylnaphthalenes (28 against 60–70). In addition there is the formation of non-recoverable heavy products, such as dinaphthylmethanes possibly with from 1 to 3 methyl groups bound to the aromatic groups.

EXAMPLE 9

4 gr of zeolite ZSM-12 (molar ratio $SiO_2/Al_2O_3$ is 100), prepared in accordance with example 1, pelleted and granulated within a range of 20–40 mesh, are charged into the isothermal zone of a fixed bed reactor, with quartz above and below as inert filler. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 35 bars. The mixture of reagents fed consists of 1,2,4-trimethylbenzene, naphthalene, 1-methylnaphthalene, methylnaphthalene, methanol in the following molar ratios: 1,2,4-trimethylbenzene/naphthalene groups=18, methanol/naphthalene=2, methanol/methylnaphthalene=1. Naphthalene groups refer to the sum in moles of naphthalene, 1-methylnaphthalene, 2-methylnaphthalene 30% of the naphthalene groups consists of naphthalene, the remaining 70% consists of 30% of 1-methylnaphthalene and 70% of 2-methylnaphthalene. At this point the mixture is heated and brought to a temperature of 300° C. In this test the conditions are therefore liquid phase, with respect to the state of reagents and products. The WHSV (hours$^{-1}$) with respect to the total mixture is 0.43. The products leaving the reactor are cooled and analyzed by gaschromatography. Samples are taken of the products at regular time intervals (time on stream). The conversion of the methanol is always total.

The selectivities calculated with respect to the naphthalene groups as if they all derived from simple naphthalene are:
selectivity dimethylnaphthalenes (% moles): 40.3
selectivity 2,6-dimethylnaphthalene (% moles): 13.3
selectivity 2,6/1,6/1,5-dimethylnaphthalene (% moles): 27.4
selectivity methylnaphthalenes moles): 56.2
selectivity polymethylnaphthalenes (% moles): 3.4
molar ratio 2,6-dimethylnaphthalene/total dimethylnaphthalenes (% moles): 33.3
molar ratio 2,6-1,6-1,5-dimethylnaphthalene/total dimethylnaphthalenes (% moles): 67.9
molar ratio 2,6/2,7 dimethylnaphthalene: 2.5

The mole % of dimethylnaphthalenes out of the total naphthalene groups is 33.2.

Under the same experimental conditions and with the same t.o.s., i.e. the deactivation of the catalyst, a mixture is reacted which differs from the previous one in that it contains naphthalene alone as naphthalene substrate. The following selectivities with respect to naphthalene correspond to a conversion of 32.9%:
selectivity dimethylnaphthalenes (% moles): 20.9
selectivity 2,6-dimethylnaphthalene (% moles): 7.1
selectivity 2,6/1,6/1,5-dimethylnaphthalene (% moles): 13.6
selectivity methylnaphthalenes (% moles): 79.1
selectivity polymethylnaphthalenes (% moles): 0.0
molar ratio 2,6-dimethylnaphthalene/total dimethylnaphthalenes (% moles): 34.2
molar ratio 2,6-1,6-1,5-dimethylnaphthalene/total dimethylnaphthalenes (% moles): 65.2
molar ratio 2,6/2,7 dimethylnaphthalene: 2.6

On comparing the two tests, it can be observed that at a certain temperature, it is possible to increase the yield to dimethylnaphthalenes substituting part of the naphthalene with methylnaphthalenes.

EXAMPLE 10

Two tests are carried out under the following conditions:

4 gr of zeolite ZSM-12 (molar ratio $SiO_2/Al_2O_3=100$), prepared in accordance with example 1, pelleted and granulated within a range of 20–40 mesh, are charged into the isothermal zone of a fixed bed reactor, with quartz above and below as inert filler. The reactor is heated to 200° C. for at least 2 hours, under a stream of nitrogen against atmospheric pressure. Maintaining under a stream of inert gas, the reactor is cooled to room temperature, and the reagents are then fed until the reactor is pressurized to 35 bars.

In the first test, the naphthalene hydrocarbon used is only naphthalene and the reagent mixture fed consists of 1,2,4-trimethylbenzene, naphthalene and methanol in the following molar ratios: 1,2,4-trimethylbenzene/naphthalene=18, methanol/naphthalene=2.

In the second test, the naphthalene hydrocarbon fed consists of 73.7% of naphthalene and the remaining 26.3% of dimethylnaphthalenes and the reagent mixture used consists of 1,2,4-trimethylbenzene, naphthalene, dimethylnaphthalenes and methanol. The methanol is charged proportionally to the naphthalene groups, according to the following criterium: 2 moles of methanol per mole of naphthalene, no mole of methanol per mole of dimethylnaphthalene. The molar ratio 1,2,4-trimethylbenzene/naphthalene groups is equal to 18. Naphthalene groups refer in this case to the sum in moles of naphthalene and dimethylnaphthalenes. The operation is carried out at a temperature of 320° C., under liquid phase conditions, at a total WHSV of 0.43 hours$^{-1}$.

The two tests are carried out so that the equivalent conversion is comparable, the equivalent conversion (% mole) referring to the ratio, multiplied by 100, between the sum of moles of methylnaphthalenes, dimethylnaphthalenes, trimethylnaphthalenes, and polymethylnaphthalenes among the products and the total moles of naphthalenes among the products, comprising therefore also the naphthalene.

The equivalent conversion is then calculated as if all the naphthalene groups fed, methylated and non-methylated, are simple naphthalene groups.

In the first test the following results are obtained:

conversion=78.4% composition of the products % mol (after removal of the 1,2,4-trimethylbenzene):

| | |
|---|---|
| naphthalene | 21.6 |
| methylnaphthalenes | 27.4 |
| dimethylnaphthalenes | 36 |
| trimethylnaphthalenes | 15 |

In the second test the results obtained are the following:

conversion=80.8% composition of the products % mol (without the benzene hydrocarbon):

| | |
|---|---|
| naphthalene | 19.2 |
| methylnaphthalenes | 25.3 |
| dimethylnaphthalenes | 39.2 |
| trimethylnaphthalenes | 16.4 |

Comparison of the data indicated in the previous tables demonstrates that the distribution of the main products in both cases is very similar and consequently the dimethylnaphthalenes fed entered the reaction cycle without simple accumulation, i.e. inert behaviour, or only additional alkylation.

These data are in accordance with a process in which contemporaneous transalkylation, deproportioning, alkylation and isomerization reactions take place.

Table A below indicates the distribution in molar % of the isomers of dimethylnaphthalene resulting from the first test, in which the substrate used was exclusively naphthalene:

TABLE A

| isomer | mol % |
|---|---|
| 2,6 | 28.6 |
| 2,7 | 16 |
| 1,3 + 1,7 | 17.5 |
| 1,6 | 27.2 |
| 1,4 + 2,3 | 3.1 |
| 1,5 | 4.7 |
| 1,2 | 3 |
| 1,8 | 0 |

Table B below indicates the distribution in molar % of the isomers of dimethylnaphthalene resulting from the second test, in which the substrate used consisted of 73.7% of naphthalene and 26.3% of dimethylnaphthalenes (the table also indicates the percentage distribution of the isomers in the dimethylnaphthalene fed)

TABLE B

| isomer | feeding mol % | products mol % |
|---|---|---|
| 2,6 | — | 22.6 |
| 2,7 | 17.2 | 13.7 |
| 1,3 + 1,7 | — | 26 |
| 1,6 | — | 21 |
| 1,4 + 2,3 | 82.8 | 10.6 |
| 1,5 | — | 3.3 |
| 1,2 | — | 2.8 |
| 1,8 | — | 0 |

Comparison between the tables shows that the 2,3-dimethylnaphthalene fully entered the reactive system; the same can be said for the 2,7 isomer, as there is no registration of its accumulation.

Table C below summarizes the molar % composition of the products relating to the two tests discussed above: the first and second columns refer respectively to the feeding of naphthalene alone as naphthalene substrate and to the composition in molar % of products and isomers obtained in the first test; the third and fourth columns refer respectively to the composition of the naphthalene substrate and the composition in molar % of products and isomers obtained in the second test.

TABLE C (composition in % moles)

| | Feeding | Products | Feeding | Products |
|---|---|---|---|---|
| Naphthalene | 100 | 21.6 | 73.7 | 19.2 |
| 1-methylnaphthalene | — | 8.5 | — | 7.7 |
| 2-methylnaphthalene | — | 18.9 | — | 17.6 |
| Methylnaphthalenes | — | 27.4 | — | 25.3 |
| Dimethylnaphthalenes | — | 36 | 26.3 | 39.2 |
| 2,6 isomer | — | 10.3 | — | 8.9 |
| 2,7 isomer | — | 5.8 | 4.3 | 5.4 |
| 1,3 + 1,7 isomers | — | 6.3 | — | 10.2 |
| 1,6 isomer | — | 9.8 | — | 8.2 |
| 1,4 + 2,3 isomers | — | 1.1 | 21.8 | 4.1 |
| 1,5 isomer | — | 1.7 | — | 1.3 |
| 1,2 isomer | — | 1.1 | — | 1.1 |
| 1,8 isomer | — | 0 | — | 0 |
| Trimethylnaphthalenes | — | 15 | — | 16.4 |

Also in this table it can be seen that 2,3-dimethylnaphthalene fully enters the reactive system; the same can be said for the 2,7 isomer, as there is no registration of its accumulation.

EXAMPLE 11

Using the same procedure as the previous example, the following experimentations are carried out at 300° C. and 35 bars. The total WHSV is 0.43 hours$^{-1}$. In the first test the naphthalene hydrocarbon used is naphthalene alone and the reagent mixture fed consists of 1,2,4-trimethylbenzene, naphthalene and methanol in the following molar ratios: 1,2,4-trimethylbenzene/naphthalene=18, methanol/naphthalene=2.

The results obtained, expressed as composition in moles, are the following:

| | |
|---|---|
| Equivalent conv. % | 67.10 |
| Naphthalene | 32.90 |
| 1-methylnaphthalene | 10.50 |
| 2-methylnaphthalene | 24.20 |
| Methylnaphthalenes | 34.80 |
| Dimethylnaphthalenes | 29.20 |
| 2,6 isomer | 9.40 |
| 2,7 isomer | 4.00 |
| 1,3 + 1,7 isomers | 4.60 |
| 1,6 isomer | 8.50 |
| 1,4 + 2,3 isomers | 0.80 |
| 1,5 isomer | 1.30 |
| 1,2 isomer | 0.50 |
| 1,8 isomer | 0.00 |
| Trimethylnaphthalenes | 3.10 |

In the second test a feeding is used which repeats the spectrum of products obtained from the first experimentation, except that:
- the 2,6-dimethylnaphthalene, 1,6-dimethylnaphthalene and 1,5-dimethylnaphthalene (belonging to the same isomerization group as defined in EP 519165) are replaced by an equal quantity in moles of naphthalene;
- the 1,3, 2,3 and 1,4 isomers (as they belong to the same isomerization group as defined in EP 519165) are replaced by the 2,3 isomer;
- the 1,7 isomer, which is not anlaytically separated from the 1,3 isomer, and cannot therefore be quantified, is substituted with the 2,3 isomer.

This second test therefore simulates a recycling of products and isomers which are different from the desired product in the synthesis reactor of 2,6-dimethylnaphthalene. The composition in % moles of the naphthalene substrate used in the second test is therefore the following:

| | |
|---|---|
| Naphthalene | 53.70 |
| 1-methylnaphthalene | 10.60 |
| 2-methylnaphthalene | 24.50 |
| Methylnaphthalenes | 35.10 |
| Dimethylnaphthalenes | 11.20 |
| 2,6 isomer | 0.00 |
| 2,7 isomer | 4.90 |
| 1,3 + 1,7 isomers | 0.00 |
| 1,6 isomer | 0.00 |
| 1,4 + 2,3 isomers | 5.70 |
| 1,5 isomer | 0.00 |
| 1,2 isomer | 0.50 |
| 1,8 isomer | 0.00 |
| Trimethylnaphthalenes | 0.00 |

The reagent mixture fed also contains 1,2,4-trimethylbenzene and methanol. The methanol is charged proportionally to the naphthalene groups, according to the following criterium: two moles of methanol per mole of naphthalene, one mole of methanol per mole of methylnaphthalene, no mole of methanol per mole of dimethylnaphthalene. The molar ratio 1,2,4-trimethylbenzene/naphthalene groups is equal to 18. Naphthalene groups refer to the sum in moles of naphthalene, methylnaphthalenes and dimethylnaphthalenes.

The results obtained in this second experimentation, expressed as composition in % moles, are indicated in Table D below, first column, where they are compared with the spectrum of products obtained starting from naphthalene alone as naphthalene substrate (second column), with the same equivalent conversion.

TABLE D

| | | |
|---|---|---|
| Equivalent conv. % | 89.00 | 89.30 |
| Naphthalene | 11.00 | 10.70 |
| 1-methylnaphthalene | 7.50 | 7.30 |
| 2-methylnaphthalene | 17.60 | 16.60 |
| Methylnaphthalenes | 25.10 | 23.90 |
| Dimethylnaphthalenes | 49.80 | 50.20 |
| 2,6 isomer | 15.00 | 15.20 |
| 2,7 isomer | 8.10 | 8.40 |
| 1,3 + 1,7 isomers | 8.50 | 8.40 |
| 1,6 isomer | 13.60 | 14.10 |
| 1,4 + 2,3 isomers | 1.50 | 1.10 |
| 1,5 isomer | 2.20 | 2.30 |
| 1,2 isomer | 1.10 | 0.70 |
| 1,8 isomer | 0.00 | 0.00 |
| Trimethylnaphthalenes | 14.10 | 15.20 |

As can be seen from the above table, from the test which simulates the recycling, there is a spectrum of products (column 1) which is practically undistinguishable from that obtained, with the same equivalent conversion, starting from naphthalene alone (column 2): these data show that the dimethylnaphthalenes fed have entered the reaction cycle, as there is no simple accumulation, i.e. inert behaviour, or only additional alkylation, and they are also in accordance with a process in which transalkylation, deproportioning, alkylation and isomerization reactions contemporaneously contribute to the formation of the desired product 2,6-dimethylnaphthalene.

EXAMPLE 12

Using the same procedure as the previous example, a test is carried out at 300° C. and 35 bars. The total WHSV is 0.43 hours$^{-1}$. Methylnaphthalene is used as naphthalene hydrocarbon, consisting of 70% of 2-methylnaphthalene and 30% of 1-methylnaphthalene. The reagent mixture fed consists of 1,2,4-trimethylbenzene, methylnaphthalene and methanol in the following molar ratios: 1,2,4-trimethylbenzene/methylnaphthalene=10, methanol/methylnaphthalene=0.5. The methylnaphthalene fed consists of 70% of 2-methylnaphthalene and 30% of 1-methylnaphthalene.

During the test two samplings are taken, with relative GC analysis of the products, and the results are indicated in the following table:

|  | time on stream (hours) | time on steam (hours) | Feeding |
| --- | --- | --- | --- |
|  | 92 | 130 | — |
| Conv. MN % | 65.9 | 64.4 | — |
| Select. DMNi (mol %) | 85.2 | 86.5 |  |
| Select. 2,6 DMN (mol %) | 29.6 | 30.2 |  |
| Select. 2,6.1,6-1,5 DMN (mol %) | 60 | 61.2 |  |
| Select. N (mol %) | 1.8 | 1.8 |  |
| Select. PMNi (mol %) | 12.9 | 11.7 |  |
| 2,6-DMN/total DMNi (mol %) | 34.7 | 34.9 |  |
| 2,6-1,6-1,5-DMN/total DMNi (mol %) | 70.4 | 70.7 |  |
| Molar ratio 2,6/2,7-DMN | 2.5 | 2.6 |  |
| Composition in weight % (solvent free) |  |  |  |
| N | 1 | 1 |  |
| 1-MN | 9.7 | 10.2 | 30 |
| 2-MN | 22.1 | 23.1 | 70 |
| MNi | 31.9 | 33.3 | 100 |
| EtNi | 0 | 0 |  |
| DMNi | 57.6 | 57.3 |  |
| 2,6-DMN | 20 | 20 |  |
| 2,7-DMN | 8 | 7.8 |  |
| 1,3-1,7-DMN | 7.6 | 7.4 |  |
| 1,6-DMN | 17.7 | 17.7 |  |
| 1,4-2,3-DMN | 0.6 | 0.6 |  |
| 1,5-DMN | 2.9 | 2.8 |  |
| 1,2-DMN | 0.8 | 1 |  |
| 1,8-DMN | 0 | 0 |  |
| TMNi | 9.5 | 8.4 |  |

In the above table N=naphthalene; MN=methylnaphthalene; MNi=methylnaphthalenes; EtNi=ethylnaphthalenes; DMN=dimethylnaphthalene; DMNi=dimethylnaphthalenes; TMNi=trimethylnaphthalenes; PMNi=polymethylnaphthalenes.

Under these conditions there is a very high selectivity to dimethylnaphthalenes, whereas the distribution of the isomers internally does not differ from the previous examples. The high total selectivity to total DMNi, is reflected in a greater weight % production of 2,6-DMN than the previous examples.

EXAMPLE 13 (comparative)

Two grams of Y zeolite (FAU) (TOSOH HSZ 330 HUA, molar ratio SiO$_2$/Al$_2$O$_3$=6), in acid form, pelleted and granulated within a range of 20–40 mesh, are charged into the isothermal zone of a fixed bed reactor, with quartz above and below as inert filler. The temperature of the reactor is brought to 200° C. for at least 2 hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1,2,4-trimethylbenzene, naphthalene, methanol in the following molar ratios: 1,2,4-trimethylbenzene/naphthalene=10, methanol/naphthalene=3. At this point the mixture is heated and brought to a temperature of 350° C. Therefore, in this test we are in the conditions of liquid phase, with respect to the state of reagents and products. The WHSV (h$^{-1}$) (with respect to the total mixture) is 0.86. The products at the output the reactor are cooled and analyzed by gaschromatography. Samples are taken of the products at regular time on stream intervals.

The conversion of the methanol is always total.

The conversion of the naphthalene after 95 h is 21.7%.

The selectivities with respect to the naphthalene are:

selectivity dimethylnaphthalenes (% moles): 14.8 selectivity 2,6-dimethylnaphthalene (% moles): 1.4 selectivity 2,6/1,6/1,5-dimethylnaphthalene (% moles): 3.9 selectivity methylnaphthalenes (% moles): 84.1 selectivity polymethylnaphthalenes (% moles): 1.1 molar ratio 2,6-dimethylnaphthalene/total dimethylnaphthalenes (% moles): 9.7 molar ratio 2,6-1,6-1,5-dimethylnaphthalene/total dimethylnaphthalenes (% moles): 26.5 molar ratio 2,6/2,7 dimethylnaphthalene: 1.1

From the results indicated above it can be observed that Y zeolite, with respect to ZSM-12 zeolite, under the same conditions, is less active, less selective to dimethylnaphthalenes, less selective to the 2,6 isomer and to the 2,6-+1,6-+1,5- isomers. In addition it is much less selective towards the formation of the 2,6 isomer with respect to the 2,7 isomer (ratio close to the thermodynamic ratio) and much less selective towards the formation of the 2,6 isomer with respect to the other isomers of dimethylnaphthalenes.

EXAMPLE 14 (comparative)

Two grams of ZSM5 zeolite (MFI) (PQ CBU3070E, ratio SiO$_2$/Al$_2$O$_3$=30), in acid form, pelleted and granulated within a range of 20–40 mesh, are charged into the isothermal zone of a fixed bed reactor, with quartz above and below as inert filler. The temperature of the reactor is brought to 200° C. for at least 2 hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1,2,4-trimethylbenzene, naphthalene, methanol in the following molar ratios: 1,2,4-trimethylbenzene/naphthalene=10, methanol/naphthalene=3. At this point the mixture is heated and brought to a temperature of 350° C. Therefore in this test the conditions are of liquid phase, with respect to the state of reagents and products. The WHSV (h$^{-1}$) (with respect to the total mixture) is 0.86. The products at the output of the reactor are cooled and analyzed by gaschromatography. Samples are taken of the products at regular time on stream intervals.

The conversion of the methanol is always total.

The conversion of the naphthalene after 49 h is 6.7%.

The selectivities with respect to the naphthalene are:

selectivity dimethylnaphthalenes (% moles): 24.5 selectivity 2,6-dimethylnaphthalene (% moles): 6.6 selectivity 2,6/1,6/1,5-dimethylnaphthalene (% moles): 6.6 selectivity methylnaphthalenes (% moles): 57.3 selectivity to ethylnaphthalenes (% moles): 18.2 selectivity polymethylnaphthalenes (% moles): 0.0 molar ratio 2,6-dimethylnaphthalene/total dimethylnaphthalenes (% moles): 27.0 molar ratio 2,6-1,6-1,5-dimethylnaphthalene/total dimethylnaphthalenes (% moles): 27.0 molar ratio 2,6/2,7 dimethylnaphthalene: 0.5

EXAMPLE 15

The experimental data obtained with ZSM-12 zeolite (prepared according to example 1) operating under the same conditions as example 2 and the previous comparative example, after 49 hours of time on stream, are provided hereunder.

Conversion of naphthalene: 75.8%.

The selectivities with respect to the naphthalene are:

selectivity dimethylnaphthalenes (% moles): 47.9 selectivity 2,6-dimethylnaphthalene (% moles): 13.8 selectivity 2,6/1,6/1,5-dimethylnaphthalene (% moles): 29.2 selectivity methylnaphthalenes (% moles): 44.3 selectivity polymethylnaphthalenes (% moles): 7.8 molar ratio 2,6-dimethylnaphthalene/total dimethylnaphthalenes (% moles): 28.9 molar ratio 2,6-1,6-1,5-dimethylnaphthalene/total dimethylnaphthalenes (% moles): 61.0 molar ratio 2,6/2,7 dimethylnaphthalene: 1.9

On comparing the above data with those of the previous example 14, it can be observed that ZSM-5 zeolite, with respect to ZSM-12 zeolite, under the same conditions, is much less active, less selective to dimethylnaphthalenes, less selective to 2,6 isomer, less selective to 2,6-+1,6-+1,5-isomers. In addition it produces a large quantity of ethylnaphthalenes, which are absent in the spectrum of ZSM-12 products. The molar ratio between 2,6 and 2,7 isomers is far from the thermodynamic ratio and is decisively unbalanced towards 2,7.

EXAMPLE 16 (comparative)

Two grams of Y zeolite (FAU) (TOSOH HSZ 330 HUA, molar ratio $SiO_2/Al_2O_3$=6), in acid form, pelleted and granulated within a range of 20–40 mesh, are charged into the isothermal zone of a fixed bed reactor, with quartz above and below as inert filler. The temperature of the reactor is brought to 200° C. for at least two hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1,2,4-trimethylbenzene and naphthalene. The molar ratio 1,2,4-trimethylbenzene/naphthalene=10. In this example methanol is not present in the reaction mixture. After pressurizing the reactor, it is heated and brought to a temperature of 350° C. Therefore, in this test the conditions are of liquid phase, with respect to the state of reagents and products. The WHSV ($h^{-1}$) (with respect to the total mixture) is 0.86. The products at the output of the reactor are cooled and analyzed by gaschromatography. Samples are taken of the products at regular time on stream intervals.

The conversion of the naphthalene after 95 h is 22.9%.

The selectivities with respect to the naphthalene are:

selectivity dimethylnaphthalenes (% moles): 15.6 selectivity 2,6-dimethylnaphthalene (% moles): 1.7 selectivity 2,6/1,6/1,5-dimethylnaphthalene (% moles): 4.4 selectivity methylnaphthalenes (% moles): 83.1 selectivity polymethylnaphthalenes (% moles): 1.3 molar ratio 2,6-dimethylnaphthalene/total dimethylnaphthalenes (% moles): 10.8 molar ratio 2,6-1,6-1,5-dimethylnaphthalene/total dimethylnaphthalenes (% moles): 28.0 molar ratio 2,6/2,7 dimethylnaphthalene: 1.0

EXAMPLE 17

Two grams of ZSM12 zeolite (MTW) (prepared as described in example 1) pelleted and granulated within a range of 20–40 mesh, are charged into the isothermal zone of a fixed bed reactor, with quartz above and below as inert filler. The temperature of the reactor is brought to 200° C. for at least 2 hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1,2,4-trimethyl-benzene and naphthalene. The molar ratio 1,2,4-trimethylbenzene/naphthalene=10. In this example methanol is not present in the reaction mixture. After pressurizing the reactor, it is heated and brought to a temperature of 350° C. Therefore in this test the conditions are of liquid phase, with respect to the state of reagents and products. The WHSV ($h^{-1}$) (with respect to the total mixture) is 0.86. The products at the output of the reactor are cooled and analyzed by gaschromatography. Samples are taken of the products at regular time on stream intervals.

The conversion of the naphthalene after 95 h is 49.5%.

The selectivities with respect to the naphthalene are:

selectivity dimethylnaphthalenes (% moles): 32.5 selectivity 2,6-dimethylnaphthalene (% moles): 9.0 selectivity 2,6/1,6/1,5-dimethylnaphthalene (% moles): 19.0 selectivity methylnaphthalenes (% moles): 64.8 selectivity polymethylnaphthalenes (% moles): 2.7 molar ratio 2,6-dimethylnaphthalene/total dimethylnaphthalenes (% moles): 27.7 molar ratio 2,6-1,6-1,5-dimethylnaphthalene/total dimethylnaphthalenes (% moles): 57.6 molar ratio 2,6/2,7 dimethylnaphthalene: 2.0

On comparing the data of example 17 above with the data of the previous comparative example 16, both carried out without methanol, it can be observed that Y zeolite, with respect to ZSM-12 zeolite, under the same conditions, is less active, less selective to dimethylnaphthalenes, less selective to 2,6 isomer and to 2,6-+1,6-+1,5- isomers. In addition it is much less selective towards the formation of 2,6 isomer with respect to 2,7 isomer (ratio close to the thermodynamic ratio) and much less selective towards the formation of 2,6 isomer with respect to the other isomers of dimethylnaphthalenes.

EXAMPLE 18 (comparative)

Two grams of ZSM12 zeolite (MTW) (prepared as described in example 1), pelleted and granulated within a range of 20–40 mesh, are charged into the isothermal zone of a fixed bed reactor, with quartz above and below as inert filler. The temperature of the reactor is brought to 200° C. for at least two hours, under a stream of nitrogen against atmospheric pressure. Maintaining under a stream of inert gas, the reactor is cooled to room temperature, and the reagents are then fed until the reactor is pressurized to 40 bars. The mixture of reagents fed consists of 1-methylnaphthalene (liquid at room temperature and also at 350° C., 40 bars) and methanol. The molar ratio methanol/1-methylnaphthalene is equal to 0.5. After pressurizing the reactor, it is heated and brought to a temperature of 350° C. The WHSV ($h^{-1}$) (with respect to the total mixture) is 0.75. The products at the output of the reactor are cooled and analyzed by gaschromatography. Samples are taken of the products at different time on stream intervals. The conversion of the methanol is always total. The conversion of 1-methylnaphthalene, after 20 hours of time on stream is equal to 16.8%.

The molar ratio 2,6-dimethylnaphthalene/total dimethylnaphthalenes is 7.7

The molar ratio 2,6-1,6-1,5-dimethylnaphthalene/total dimethylnaphthalenes is 25.7

The molar ratio 2,6/2,7 dimethylnaphthalene is 0.9

The conversion of 1-methylnaphthalene, after 23 hours of time on stream is equal to 12.0%.

The molar ratio 2,6-dimethylnaphthalene/total dimethylnaphthalenes is 6.1

The molar ratio 2,6-1,6-1,5-dimethylnaphthalene/total dimethylnaphthalenes is 27.1

The molar ratio 2,6/2,7 dimethylnaphthalene is 1.0

What is claimed is:

1. A process for preparing 2,6-dimethylnaphthalene which comprises subjecting 1,6 and/or 1,5-dimethylnaphthalenes, optionally mixed with other isomers of dimethylnaphthalene, to isomerization, which comprises treating said compounds at a temperature ranging from 100 to 400° C., under at least partially liquid phase conditions, in the presence of an MTW zeolite, thereby producing a product comprising 2,6-dimethylnaphtalene.

2. The process according to claim 1, wherein the temperature ranges from 120 to 250° C.

* * * * *